(12) United States Patent
Berends et al.

(10) Patent No.: US 9,410,138 B2
(45) Date of Patent: Aug. 9, 2016

(54) ASPARAGINASE FROM BASIDIOMYCETES

(71) Applicant: NESTEC S.A., Vevey (CH)

(72) Inventors: Pieter Berends, Zoznegg-muhlingen (DE); Swen Rabe, Muehlingen (DE); Ralf Gunter Berger, Hannover (DE); Diana Linke, Bad Rehburg (DE); Nadine Eisele, Kufstein (AT)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/477,448

(22) Filed: Sep. 4, 2014

(65) Prior Publication Data

US 2015/0093472 A1    Apr. 2, 2015

Related U.S. Application Data

(62) Division of application No. 13/810,134, filed as application No. PCT/EP2011/055375 on Apr. 6, 2011, now abandoned.

(30) Foreign Application Priority Data

Jul. 14, 2010   (EP) .................................... 10169405

(51) Int. Cl.
   *C12N 9/82*   (2006.01)
   *A23L 1/015*  (2006.01)
   *A23K 1/00*   (2006.01)

(52) U.S. Cl.
   CPC . *C12N 9/82* (2013.01); *A23K 1/006* (2013.01); *A23L 1/0153* (2013.01); *A23V 2002/00* (2013.01)

(58) Field of Classification Search
   None
   See application file for complete search history.

(56) References Cited

U.S. PATENT DOCUMENTS

2004/0058054 A1   3/2004   Elder et al.
2007/0026511 A1   2/2007   Morrissey et al.

FOREIGN PATENT DOCUMENTS

| JP | 62012720 | 1/1987 | |
| JP | 63060915 | 3/1988 | |
| JP | 10057080 | 3/1998 | |
| JP | 2004283062 | 10/2004 | |
| NL | WO 2008128975 A1 * | 10/2008 | ............ A23L 1/0153 |
| WO | 2008/128975 | 10/2008 | |

OTHER PUBLICATIONS

Hanne V. Hendricksen et al. "Evaluating the Potential for Enzymatic Acrylamide Mitigation in a range of Food Products Using an Asparaginase from Aspergillus oryzae," Apr. 23, 2009, pp. 5168-4178.
XP002652928, Oct. 2007, pp. S196-S197.
Garren "Studies on Polyporus Abietinus I. The Enzyme-Producing Ability of the Fungus" Phytopathology, vol. 28, No. 1, Jan. 1938, pp. 839-845.
Sato et al. "*Cryptococcus nodaensis* sp nov, a yeast isolated from soil in Japan that produces a salt-tolerant and thermostable glutaminase" Journal of Industrial Microbiology & Biotechnology, vol. 22, 1999, pp. 127-132.
Kohlmunzer et al. "Badanie aktywnosci L-asparaginazy w niektorych krajowych gatunkach grzybow wyzszych" Herba Polonica, vol. 26, No. 4, 1980, pp. 227-231.
Ramakrishnan et al. "Characterization of an extracellular asparaginase of Rhodosporidium toruloides CBS14 exhibiting unique physicochemical properties" Canadian Journal of Microbiology, vol. 42, No. 4, Apr. 1996, pp. 316-325.
Eisele et al. "The first characterized asparaginase from a basidiomycete, Flammulina velutipes" Bioresource Technology, vol. 102, 2011, pp. 3316-3321.
Smiderle et al. "Structural characterization of a polysaccharide and a beta-glucan isolated from the edible mushroom Flammulina velutipes" Science Direct, Phytochemistry, vol. 67, 2006, pp. 2189-2196.
Chilean Office Action for Application No. 3490-2012, dated Aug. 25, 2015, 8 pages.
Kuilman et al. "Safety of the enzyme asparaginase, a means of reduction of acrylamide in food" Abstracts / Toxicology Letters, 172S (2007)—pp. S196-S197.
Hendriksen et al. "Evaluating the Potential for Enzymatic Acrylamide Mitigation in a Range of Food Products Using an Asparaginase from Aspergillus oryzae" Journal of Agricultural and Food Chemistry, 2009, vol. 57, pp. 4168-4176.
International Search Report & Written Opinion issued Sep. 2, 2011 for Intl. Appln. PCT/EP2011/055375.

* cited by examiner

*Primary Examiner* — Paul Holland
(74) *Attorney, Agent, or Firm* — K&L Gates LLP

(57) ABSTRACT

An asparaginase enzyme derived from the fungi Basidiomycete, in particular the Basidiomycete is *Flammulina velutipes*. A method for hydrolysing at least one of L-asparagine or L-glutamine. A method for reducing acrylamide formation in a substance comprising L-asparagine is also described.

4 Claims, 5 Drawing Sheets

A

```
  1 atgaaatctt ttgccctctt cgtccctctc atcgttgctg ctgtcgtcaa
 51 cagcgccgtg gtcaccttt ccacggcct tggctgcaac tctgtctcgc
151 agacctaccg tggcaactgc aacttctgcg ctgacccacc cggcggtagg
101 tctacttcac attgatccct atagctcgat gctcatctca tctactagac
201 tggagctcag tcggcttttc tgagatcgga ggcgacaacc gcgtcaccgt
251 tcataaccag aacagctgca ccccgcttc gcaggtcggc caaggctttg
301 gaccggcctg ctggaaccaa ggcgctacca agcttcgttc tgcttgggtt
351 gcgtgccctg gacagaggtg agtcggttct ctgcagcttc ttcttttggt
401 ttacgaacga tgccactaga ctcgctgaga acggtaccat cgtcgacgac
451 gacggcgcct tcatcgactt tgcttga
```

B

```
  1 atgaaatctt ttgccctctt cgtccctctc atcgttgctg ctgtcgtcaa
 51 cagcgccgtg gtcaccttt ccacggcct tggctgcaac tctgtctcgc
151 agacctaccg tggcaactgc aacttctgcg ctgacccacc cggcgactgg
101 agctcagtcg gcttttctga gatcggaggc gacaaccgcg tcaccgttca
201 taaccagaac agctgcaccc cgcttcgca ggtcggccaa ggctttggac
251 cggcctgctg aaccaaggc gctaccagc ttcgttctgc ttgggttgcg
301 tgcctggac agagactcgc tgagaacggt accatcgtcg acgacgacgg
351 cgccttcatg gactttgctt ga
```

C

```
  1 MKSFALFVPL IVAAVVNSAV VTFSTGLGCN SVSQTYRGNG NFCADPPGDW
 51 SSVGFSEIGG DNRVTVHNQN SCTPASQVGQ GFGPACWNQG ATKLRSAWVA
101 CPGQRLAENG TIVDDDGAFI DFA
```

FIG. 3

ASPARAGINASE FROM BASIDIOMYCETES

PRIORITY CLAIM

This application is a divisional of U.S. application Ser. No. 13/810,134, filed Jan. 14, 2013 and now abandoned, which is a U.S. national stage filing of International Appl. No. PCT/EP2011/055375, filed Apr. 6, 2011, which claims priority to European Patent Appl. No. 10169405.7, filed Jul. 14, 2010, the entire contents of which are expressly incorporated herein by reference thereto.

FIELD OF THE INVENTION

The field of the present invention relates to an asparaginase enzyme obtainable from the fungi Basidiomycetes, esp. Basidiomycetes *Flammulina velutipes*. A method for the hydrolysis of L-asparagine and L-glutamine are also disclosed. A method for reducing the formation of acrylamide in a substance comprising L-asparagine is also disclosed.

BACKGROUND OF THE INVENTION

Applications of asparaginase enzymes in food technology originate from the finding that a thermal treatment of food converts asparagine in the presence of reducing carbohydrates partly to acrylamide. Since carbohydrates are as ubiquitous as amino acids in food, there is a permanent risk of generating the cancerogenic and genotoxic acrylamide during the thermal treatment of food. The thermal treatment is for example a baking, a roasting, a barbecuing or a deep-fat frying of the food. The onset of acrylamide formation during the thermal treatment of the food is observed at temperatures exceeding 120° C. The Joint FAO/WHO Expert Committee on Food Additives (JECFA) has stated that dietary exposure to acrylamide may indicate a human health concern given its genotoxicity and carcinogenicity.

Particular concerns in the food industry arise for the numerous varieties of for example breads, cookies, snacks, biscuits, cereals, roasted seeds (such as cocoa, coffee), extruded and cut potato products that need to be inherently thermally treated.

The thermal treatment of the food is indispensible for a quality of the food. For example the browning (Maillard) reaction in the food forms the typical flavours, colours, and antioxidants in the food. Furthermore microbial safety and extended shelf-life of the food are achieved due to the thermal treatment of the food.

It would be desirable to enable a selective removal of L-asparagine prior to the thermal treatment of the food.

Genetic engineering of potato using an antisense asparagine synthase gene and tuber specific promoters have been reported to reduce, but not to eliminate asparagine from the potato tuber (Rommens 2007); a full elimination of asparagine is supposedly lethal for the plant.

Enzymes are ideal selective tools to modify a food constituent without affecting other food constituents. A catalytic action of enzymes on the food is distinguished by a high substrate plus reaction specificity and by gentle physical conditions of enzyme action. The enzyme action on the food is more environmentally friendly as no organic solvents or heavy metals are involved ("green chemistry"; "white biotechnology"). Enzymes used to modify the food constituent allow changing a single food constituent whilst avoiding any side-reactions which could eventually result in the formation of toxic compounds in the food.

However, no enzyme technology can be currently envisaged for the selective hydrolysis of a protein bound amino acid, such as asparagine, from a food protein, even less while maintaining the typical structural and sensory properties of the respective food material.

It would be desirable to hydrolyse e.g. free and mobile asparagine in the food to aspartic acid. The asparagine cannot then serve as a precursor molecule for acrylamide formation when the food is thermally treated.

STATE OF THE ART

Asparaginase (EC 3.5.1.1; L-asparagine amidohydrolases) is an enzyme that catalyses the hydrolysis of L-asparagine to aspartic acid with the liberation of ammonia. By definition asparaginase enzymes act on a nitrogen-carbon bond in linear amides, but not on peptide bonds of the L-asparagine.

L-asparagine was the first amino acid detected (1806 in the juice of *Asparagus officinalis*) and L-asparagine is ubiquitous in all living cells. Accordingly, asparaginase enzymes occur abundantly in nature from prokaryotic microorganisms to vertebrates; see Halpern, Y. S. and Grossowicz, N., Hydrolysis of amides by extracts from mycobacteria, Biochem. J. 65: 716-720 (1957); Ho, P. P. K., Frank, B. H. and Burck, P. J., Crystalline L-asparaginase from *Escherichia coli* B., Science 165: 510-512 (1969); Suld, H. M. and Herbut, P. A., Guinea pig serum and liver L-asparaginases—Comparison of serum and papain-digested liver L-asparaginase. J. Biol. Chem. 245: 2797-2801 (1970). The tetramer asparaginases from *E. coli* with 326 amino acids (Jackson, R. Ch. and Handschumacher, R. E., *Escherichia coli* L-asparaginase. Catalytic activity and subunit nature, Biochemistry, 1970, 9 (18), pp 3585-3590) were the first to be examined in detail.

Until recently L-asparaginase is used as a cytostaticum in cancer therapy to fight leukemia cells and mast cell tumors (Herbert F. Oettgen, L-Asparaginase: Ein neues Prinzip in der Chemotherapie maligner Neoplasien, Annals of Hematology, 1969, 19(6), 351-356).

More recently asparaginase enzymes were reported to be derived from bacteria (*Helicobacter pylori*, Scotti et al. 2010; *Pyrococcus furiosus*, Greiner-Stoeffele and Struhalla, 2008) and from molds (*Aspergillus niger*, Van der Laan et al. 2008; *Aspergillus oryzae*, Matsui et al. 2008). The addition of di- and tri-valent cations and various amino acids and free thiols (Elder et al. 2007), or of alpha-amylase (de Boer, 2006), or of calcium chloride in conjunction with phosphoric or citric acid (Elder et al. 2005) was claimed to support somehow the activity of the asparaginase enzyme.

A Glutaminase enzyme is related to the asparaginase enzyme. The glutaminase enzyme is typically derived from either lactic acid bacteria as they, for example, occur in the chicken intestinal flora (Thongsanit et al. 2008; *Lactobacillus rhamnosus*, Weingand-Ziade et al. 2003), or from yeasts (*Zygosaccharomyces rouxii*, Iyer and Singhal 2010), or from marine fungi (*Beauveria bassiana*, Sabu et al. 2002), or again from *Aspergillus* molds (Prasanth et al. 2009).

A concerted use of the asparaginase enzyme in food technology is rather recent. In 2007 PreventAse (DSM) enzyme was introduced on the European market. The PreventAse (DSM) enzyme is produced by a recombinant mold, *Aspergillus niger*. A competing asparaginase enzyme, called Acrylaway (Novozymes), has been obtained from a related mold species, *Aspergillus oryzea* by using submerged feed-batch fermentation of a genetically modified strain carrying a gene coding for an asparaginase enzyme from *Aspergillus oryzae*. Both Aspergilli (*Aspergillus niger* and *Aspergillus oryzae*) are described as having a long history of safe industrial use, being widely distributed in nature and being commonly used for production of food-grade enzymes.

In baking applications, the asparaginase enzyme is typically mixed with the dough before the thermal treatment of the food (for example baking) to eliminate acrylamide formation. For French fries, the dipping or spraying of potato pieces in or with a solution of the asparaginase enzyme solution may be used. Such a treatment may be very efficient. In potato chip manufacture, Corrigan (2008) reported a decrease of acrylamide levels in the finished product from 1688μg/kg down to 60μg/kg in comparison to untreated potato chips. A reduction of the formation of acrylamide by >99.9% was supposed to be feasible (Elder et al. 2004).

Product safety in terms of the asparaginase enzyme applied to food is not an issue, as the asparaginase enzyme will be heat-inactivated by the thermal treatment of the food in the step before packaging. Therefore the asparaginase enzyme will unlikely come into contact with a consumer in its active form.

Enzymes from Basidiomycetes

Most of the around 1,000 edible fungi belong to the class of Basidiomycota (Basidiomycetes). Basidiomycetes are often referred to as higher fungi. Basidiomycetes reproduce by forming pillar-like cells carrying four meiospores. The anatomy of Basidiomycetes was name-giving (lat. Basidium=pillar). Basidiomycetes are appreciated all over the world by their rich flavour, a high protein and a high fiber content together with low energy. The Asian cultures additionally assign distinct health protecting and healing activities to many of the Basidiomycetes fungi.

Saprotrophic Basidiomycetes commonly inhabit forest detritus, forest soils, leaf litter, and fallen trees. The vegetative cells spread out in the sub-terranean sphere forming long filamentous cells (hyphae). To survive on the most recalcitrant organic material on earth, the three-dimensional lignin network, they possess a remarkably potent set of oxidoreductases. Among the oxidoreductases are lignin peroxidase, manganese peroxidase, versatile peroxidase, H2O2 producing oxidases such as glucose oxidase, and phenol-oxidases of the Laccase type. Glycosidases, such as cellulases, are also found and help to degrade the cellulose portion of wood.

As deciduous and coniferous wood does not contain a significant amount of protein and amino acids, an occurrence of a asparaginase enzyme activity in a fungi growing in this particular natural habitat would not be envisaged.

Cultivars of *Flammulina velutipes* from the Basidiomycetes are also known as known as Enokitake, golden needle mushroom or velvet foot. The *Flammulina velutipes* form long, thin white fruiting bodies are used in Asian cuisines as versatile mushrooms. The mushroom is traditionally used fresh, canned for soups, salads and other dishes. The mushroom can be refrigerated for about one week.

OBJECT OF THE INVENTION

An object of the present invention is to provide an asparaginase enzyme with a high activity and a high operational stability.

A further object of the present invention is to reduce the formation of acrylamide in a food product by use of the asparaginase enzyme.

SUMMARY OF THE INVENTION

In an aspect of the present invention, the invention relates to an asparaginase enzyme obtainable from Basidiomycete. In particular the Basidiomycete *Flammulina velutipes*.

In a further aspect the present invention relates to a method for hydrolysing at least one of L-asparagine or L-glutamine. The method comprises treating a substance comprising at least one of L-asparagine or L-glutamine with the asparaginase enzyme obtainable from Basidiomycete.

In a further aspect the present invention relates to a method for reducing acrylamide formation in a substance that comprises L-asparagine. The method comprises applying to the substance that comprises the L-asparagine the asparaginase enzyme obtainable from Basidiomycete. The method then comprises heating the substance comprising the L-asparagine.

The substance comprising at least one of L-asparagine or L-glutamine can be a food product.

The invention further relates to the products obtained by the methods of the present invention.

BRIEF DESCRIPTION OF THE FIGURES

The present invention is described hereinafter with reference to some embodiments as shown in the following figures wherein:

FIG. 3 shows a genomic nucleotide sequence (A; SEQ ID NO: 11), a coding nucelotide sequence (B; SEQ ID NO: 12), and the amino acid sequence (C; SEQ ID NO: 1) of the asparaginase enzyme of Flammulina velutipes. The first 19 amino acids were identified as signal sequence.

DETAILED DESCRIPTION

For a complete understanding of the present invention and the advantages thereof, reference is made to the detailed description of the invention taken in conjunction with the figures.

It should be appreciated that various aspects of the present invention are merely illustrative of the specific ways to make and use the invention and do not limit the scope of the invention when taken into consideration with the claims and the following detailed description.

In the present invention, the term asparaginase enzyme is used to refer to an enzyme that is capable of hydrolysing both L-asparagine and L-glutamine.

An aim of the present invention is to significantly reduce the formation of carcinogenic acrylamide in thermally treated food by a concerted enzymatic hydrolysis of the acrylamide precursor, L-asparagine with the asparaginase enzyme.

In an embodiment of the present invention a method for the manufacture of the asparaginase enzyme is disclosed. The asparaginase enzyme possesses operational stability and is obtained from mycelium of the Basidiomycetes *Flammulina velutipes*.

A strain of the *Flammulina velutipes* is commercially available through culture collections, such as the DSMZ (Deutsche Sammlung für Mikroorganismen and Zellkulturen GmbH, Braunschweig, Germany) or the CBS (Centraalbureau voor Schimmelcultures, Utrecht, The Netherlands).

The use of mycelium of the Basidiomycetes *Flammulina velutipes* offers great advantages in terms of ease of production and cultivation, as the collection of fruiting bodies from the wilderness is not required. As a result of the extensive use of this species Basidiomycetes *Flammulina velutipes* as a foodstuff, there are no visible health risks or safety concerns.

The fungus of the Basidiomycetes *Flammulina velutipes* can be easily grown in a submerged culture with minimum demands for medium supplements. An organic carbon source, a nitrogen source, and a phosphorous source have to be present; these sources are typically provided by natural mixtures such as a yeast extract or glucose plus inorganic ammonium and phosphate salts. A mixture of minor and trace elements, are recommended in all nutrient media of microorganisms, is added. The cultivation of the Basidiomycetes *Flammulina velutipes* is preferably carried out in a submerged culture for 3 to 20 days, preferably for 6 to 15 days. A temperature during cultivation of the Basidiomycetes *Flammulina velutipes* is typically in a range from 10 to 35° C., preferably from 20 to 30° C. A pH of about 4 to 8 is typical, with a pH of about 5 to 7 being preferred. Furthermore conditions of low light are typical of the method.

The method of biomass and asparaginase enzyme production operates under mild conditions and is environmentally friendly in contrast to the methods of the prior art.

Figure 1:
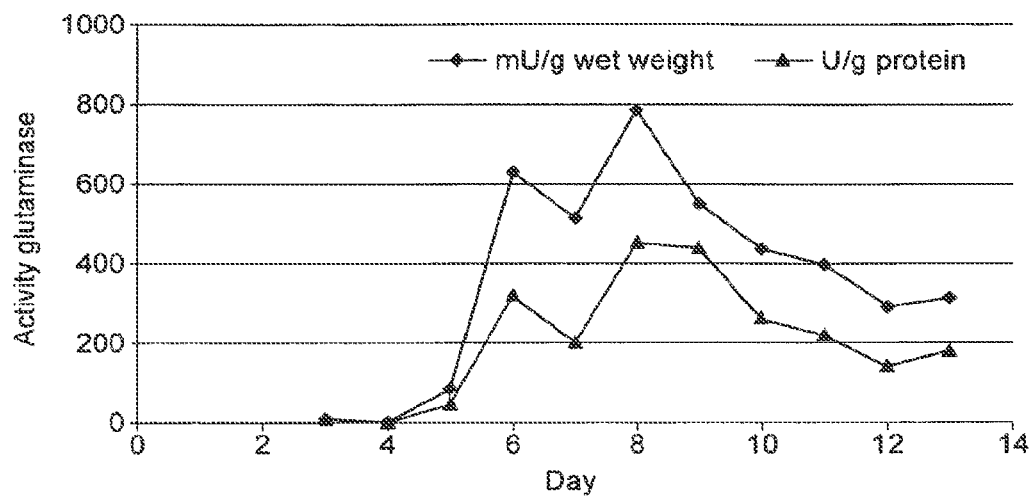
FIG. 1 shows a time course of intracellular formation of asparaginase enzyme of *Flammulina velutipes* grown in a submerged culture.
Figure 2:
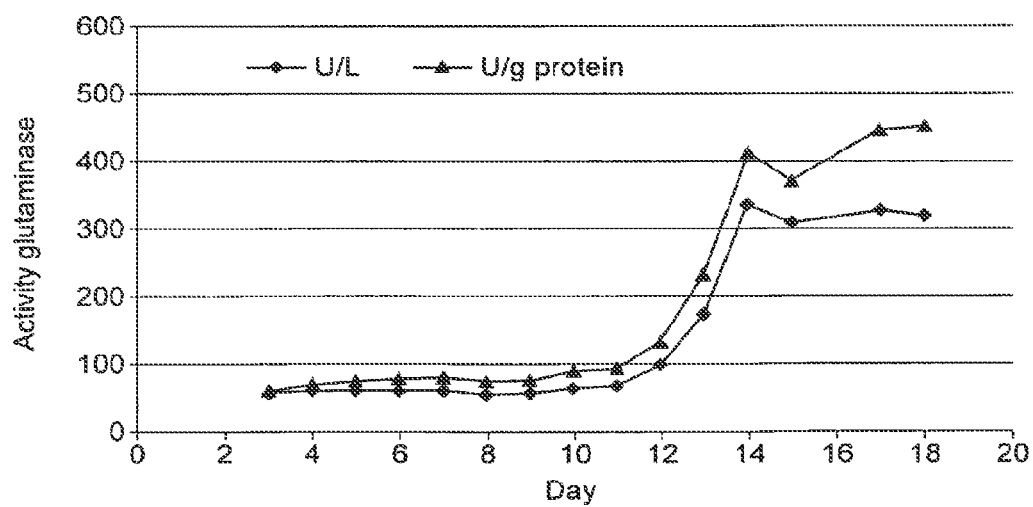
FIG. 2 shows a time course of extracellular formation of the asparaginase enzyme of *Flammulina velutipes* grown in submerged culture.
Figure 4:
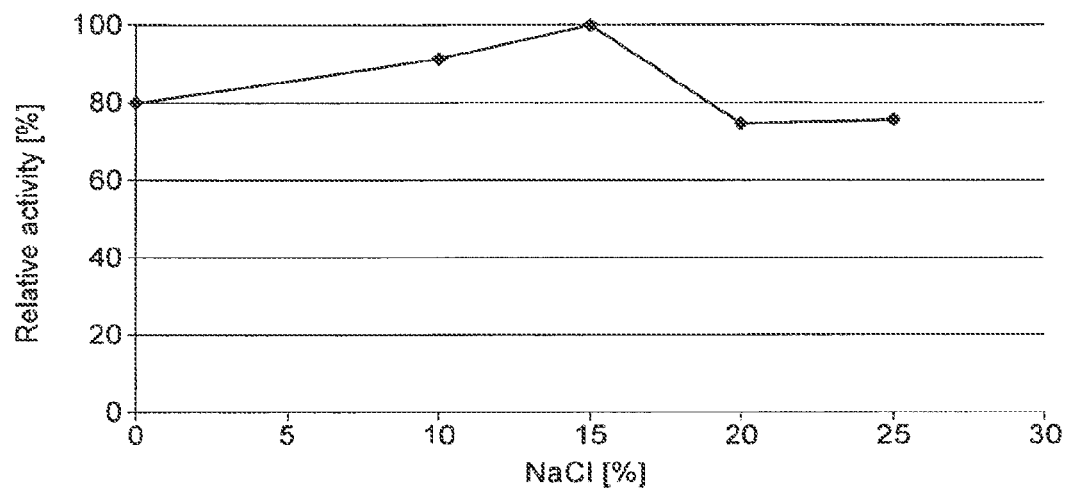
FIG. 4 shows a salt tolerance of the asparaginase enzyme from *Flammulina velutipes*, expressed in *E. coli* as a heterologous host and used as a crude enzyme.

The asparaginase enzyme activity is first accumulated intra-cellularly as shown in FIG. 1 and then secreted into a nutrient medium as shown in FIG. 2.

The nutrient medium facilitates a handling of the method as well as asparaginase enzyme isolation and enrichment using techniques known in the art. The techniques can be ultra-filtration, precipitation or adsorption. A cell-free, concentrated culture supernatant of asparaginase enzyme may thus be obtained and further used for technical hydrolysis. Although the asparaginase enzymes may be isolated by techniques known in the art, it is not necessary to do so, and a crude mixture of the asparaginase enzyme obtained may also be further used in the present method.

In the course of a submerged cultivation of *Flammulina velutipes* a peak of intracellular asparaginase enzyme activity was found after approximately one week. An excretion into the extracellular space started after 12 days and peaked after approximately 14 days.

Figure 8:
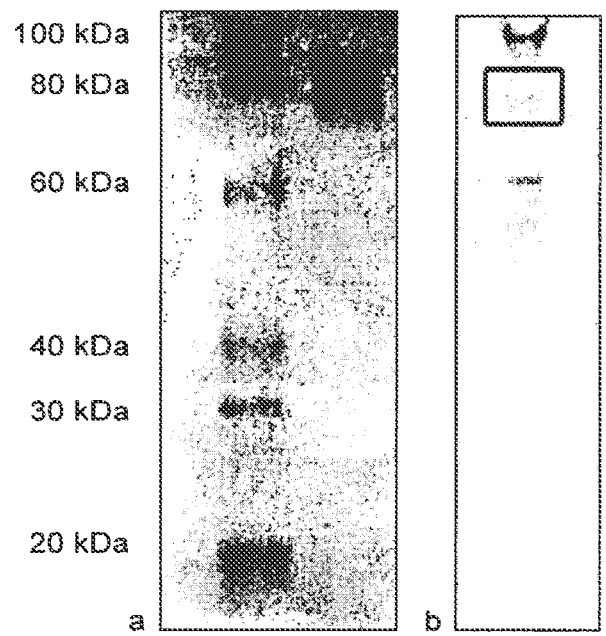
FIG. 8 shows a) activity stained native polyacrylamide gel electrophoresis (PAGE) and b) denaturing-PAGE separations of asparaginase enzyme of *Flammulina velutipes*.
Figure 9:
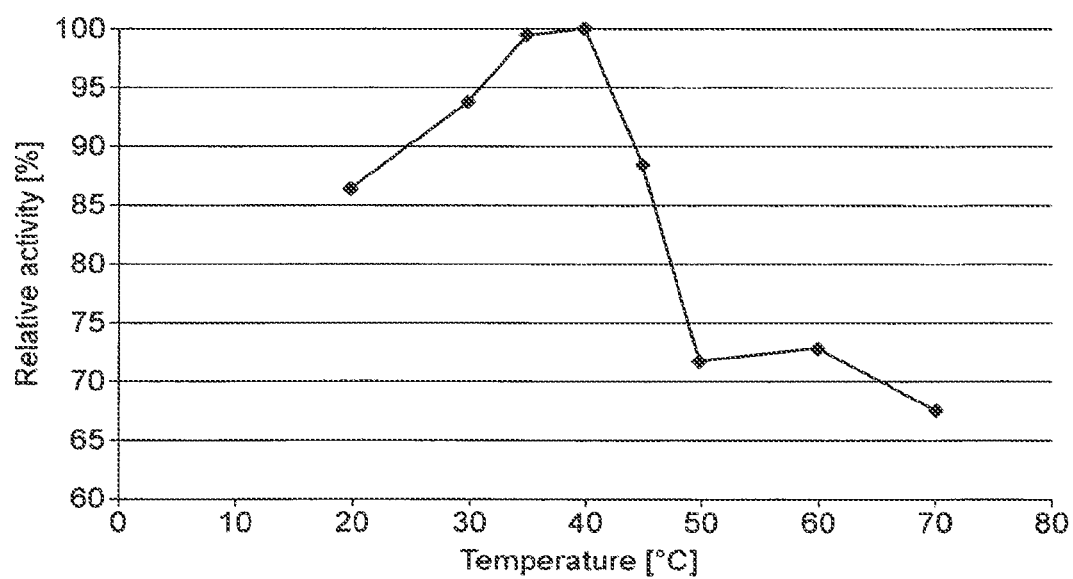
FIG. 9 shows a temperature optimum of the asparaginase enzyme of *Flammulina velutipes*.

As seen in FIG. 8, activity staining on a native poly-acrylamide gel confirmed the catalytic specificity and showed active bands of the purified enzyme at 13 and 74 kDa indicating the presence of an oligomer form besides the monomer.

If a maximum purity of the asparaginase enzyme is required, a recombinant product from *Bacillus subtilis* may be used. To develop recombinant strains, the full amino acid sequence of the asparaginase enzyme needs to be known. The full amino acid sequence of the asparaginase enzyme is shown in FIG. 3 which shows the full sequence with all 123 amino acid moieties, as deduced from the full 372 base pair sequence of the structural gene. An 18 base pair signal sequence precedes the coding region.

The asparaginase enzyme is added to a substrate. By adding the asparaginase enzyme to the substrate it is intended that the asparaginase enzyme contacts the substrate. This can include for example spraying, dipping or coating the substrate with the asparaginase enzyme. The substrate is preferably a food material that comprises any one of L-asparagine or L-glutamine. The asparaginase enzyme is usually applied to the substrate at concentrations at a total level of 1 to 200 millimolar, preferably 10 to 20 millimolar depending on the specific activity. The asparaginase enzyme can be added as the pure protein. Alternatively the asparaginase enzyme can be tailored according to the intended use by adding ingredients to the asparaginase enzyme, such as lactose, glycerol or albumin to facilitate dosage. The manufactured asparaginase enzyme or the tailored asparaginase enzyme can be in the form of, an enzyme tablet, a granulate, a stabilized liquid or a paste-like preparation.

A hydrolysis of the substrate is performed to obtain the substrate with a significantly lower levels of asparagine or glutamine as compared to the substrate prior to treatment. The conditions which may be used for the hydrolysis are standard, and can be easily determined by a person of skill in the art.

As the asparaginase enzyme activity is not affected by the chemical environment in which it is present, the substrate to be treated may be, for example:
  Beverages
  Cocoa beans
  Cheese
  Coffee beans
  Confectionery
  Desserts
  Doughs
  Dressings
  French fries
  Fruit drinks
  Meat products
  Medical diets
  Nutritional supplements
  Pet food
  Potato chips
  Sauces
  Snacks
  Soups In particular the substrate is any item consumable by a human or an animal.

The degree of hydrolysis of the asparagine in the substrate can be either assessed by measuring asparagine decrease, aspartic acid or ammonia increase or, after processing the food, by measuring a level of any residual acrylamide.

The advantage provided by the invention is that the resulting novel asparaginase enzyme has a distinct affinity and improved efficacy for the hydrolysis of L-asparagine.

Even more surprising is the excellent technical properties of the asparaginase enzyme with regards to operational stability that enables the use in processes with elevated temperature and ionic strength and different conditions of pH (FIG. 4-7). No additive or further co-substrates other than water are necessary.

Figure 5:
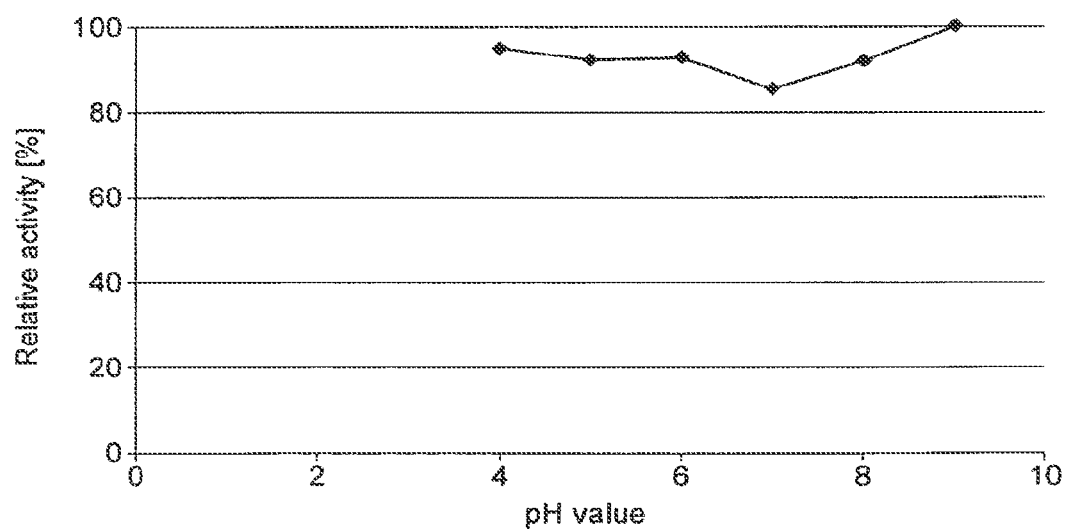
FIG. 5 shows a pH stability of the asparaginase enzyme of *Flammulina velutipes*, expressed in *E. coli* as a heterologous host and used as a crude enzyme.
Figure 6:
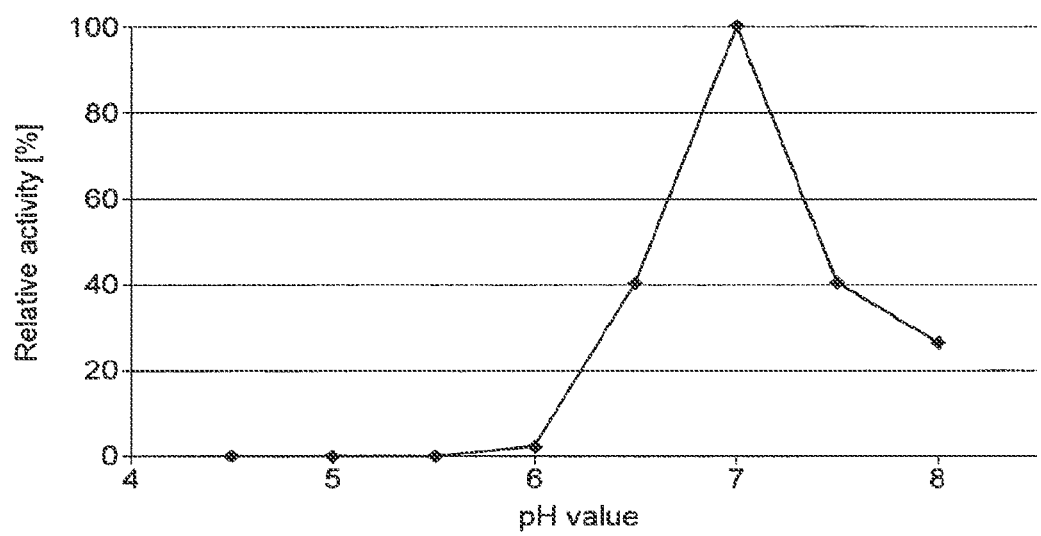
FIG. 6 shows a pH-optimum of the asparaginase enzyme of *Flammulina velutipes*.

The novel asparaginase enzyme possesses good pH stability and a broad pH-optimum between pH 5.5 and 9, see FIGS. 5 and 6. The pH of most foods is found in this range.

Figure 7:
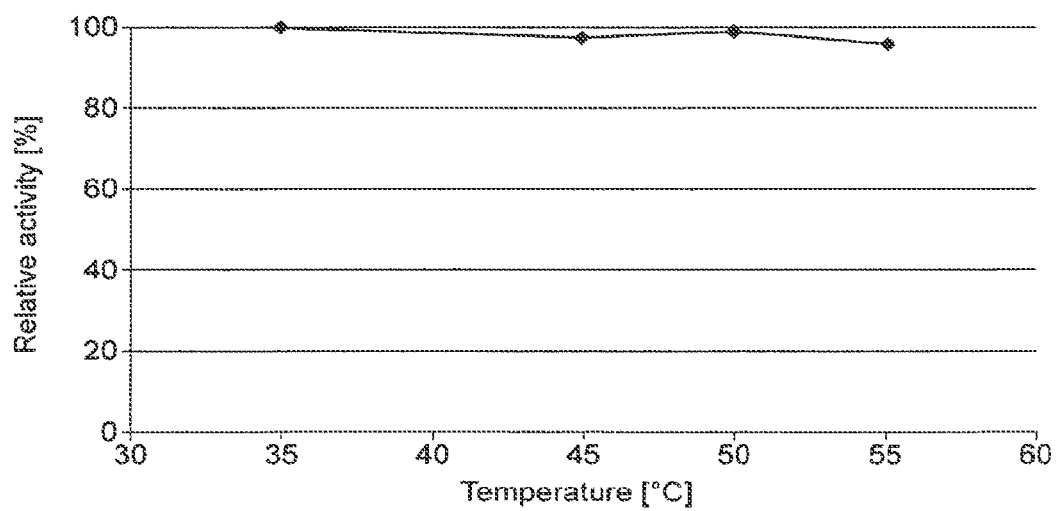
FIG. 7 shows a temperature stability of the asparaginase enzyme of *Flammulina velutipes*, expressed in *E. coli* as a heterologous host and used as a crude enzyme.

An operational stability of the asparaginase enzyme is not decreased even at temperatures as high as 55° C., see FIG. 7.

An iso-electric point of the asparaginase enzyme monomer and oligomer is near 5.2, as determined by isoelectric focussing gel electrophoresis. The molecular masses of the asparaginase enzyme monomer and oligomer are 12.8, as deduced from the full sequence and around 74 for the aggregated form, as deduced from native polyacrylamide gel electrophoresis (PAGE), see FIG. 8.

The unique sequence of the asparaginase enzyme as shown in FIG. 3 was determined by ESI-MS analysis. The best homologies of the initially found peptides were found to a carboxylase/metallo-peptidase (E-value>30), a lipase/esterase/deacetylase (E-value>100), and to a pepsin-like aspartic/glycoside hydrolase (E-value>14). The generally inhomogeneous results and poor E-values indicate that this asparaginase enzyme is without precedent and novel indeed. This is explained by the unique source, the basidiomycete species.

The present invention is described further herein by way of illustration in the following non-limiting examples.

EXAMPLES

In the following examples, materials and methods were used as outlined.

Materials and Methods

Cultivation of *Flammulina velutipes*

All media and equipment were autoclaved prior to use and standard sterilisation techniques were applied throughout the procedure. *Flammulina velutipes* was maintained on standard agar plates (30.0 g $L^{-1}$ glucose-monohydrate; 4.5 g $L^{-1}$ asparagine-monohydrate; 1.5 g $L^{-1}$ $KH_2PO_4$; 0.5 g $L^{-1}$ $MgSO_4$; 3.0 g $L^{-1}$ yeast extract; 15.0 g $L^{-1}$ agar agar; 1.0 mL $L^{-1}$ trace metal solution containing 0.005 g $L^{-1}$ $CuSO_4.5H_2O$, 0.08 g $L^{-1}$ $FeCl_3.6H_2$, 0.09 g $L^{-1}$ $ZnSO_4.7H_2O$, 0.03 g $L^{-1}$ $MnSO_4.H_2O$ and 0.4 g $L^{-1}$ EDTA (Ethylene diamine tetra acetic acid). The pH of the medium was adjusted to a pH 6 with 1 M NaOH prior to sterilisation.

Precultures were prepared by homogenisation of a 10×10 mm agar plug with mycelium of *Flammulina velutipes* in 100 mL of sterile standard nutrition solution using an Ultra Turrax (Miccra D-9, Art, Müllheim, Germany). Submerged cultures were maintained at 24° C. and 150 rpm. After cultivation for 5 days, 50 ml preculture were transferred into 250 ml main culture medium consisting of minimal medium (1.5 g L−1 KH2PO4; 0.5 g L−1 MgSO4; 1.0 ml L−1 trace metal solution) and 40 g L−1 gluten or 10 mM glutamine, respectively.

Asparaginase Enzyme Preparation from *Flammulina velutipes*

After 18 days of cultivation, the culture was filtrated and the extracellular asparaginase enzyme-containing supernatant (200 mL) was reversed foamed [1]. The retentate was concentrated using ultra-filtration with a MWCO of 10,000 kDa (Millipore, Bedford, Mass.) and separated via size exclusion chromatography at a Superose 6 with 200 mM Tris/HCl pH 7.5.

Activity Test 10 mM L-glutamine or 10 mM L-asparagine in 0.1 M potassium phosphate pH 7.0, respectively, were preheated to 37° C. The resulting assay was started by addition of 50 μl native or 10 μl recombinant enzyme in a total reaction volume of 150 μL and stopped after 10-20 min by addition of 20 μL 3% TCA or by heating at 95° C. for 10 min. A control experiment was carried out without amino acids. Formation of product was followed using HPLC. One unit of enzyme activity was calculated as the amount of enzyme required to produce 1 μM glutamic acid or aspartic acid respectively, at 37° C. per minute.

HPLC was performed using a C18 Nucleodur Pyramid, 5 μm, 4 mm ID column, methanol as eluent A, 0.1 M sodium acetate plus 0.044% triethylamine (pH adjusted to 6.5 with HCl) as the eluent B, o-phthaldialdehyde as the derivatisation reagent, and a fluorescence detector.

Free Protein

The protein concentration in the hydrolysis supernatant was estimated according to the Lowry-method using bovine serum albumin as a standard.

Temperature and pH Optima

The determination of the temperature and pH optima of the asparaginase enzyme was performed with enzyme solutions harvested during the cultivation, or after the recombinant protein was available in a soluble form. The pH optimum was examined in the range of pH 4 to 9 (0.1 M sodium acetate pH 4, 5; 0.1 M potassium phosphate pH 6, 7, 8; 0.1 M sodium carbonate pH 9) at 37° C. The optimal temperature determination ranged from 20 to 70° C. at optimal pH.

Temperature and pH Stability

To determine the pH stability 10 μL of the recombinant enzyme were incubated for 16 h at 37° C. in 40 μL of the respective buffer above. 100 μL of 10 mM glutamine in 0.1 M potassium phosphate (pH 7) was added and the reaction was incubated for 20 min at 37° C. A control experiment was carried out without substrate. The reaction was stopped at 95° C. for 10 min. The generated glutamic acid was calculated after HPLC analysis as described above.

For analysis of temperature stability 10 μL of the recombinant enzyme were incubated for 1 h at the respective ° C. in 40 μL of 0.1 M potassium phosphate buffer (pH 7). Afterwards, 100 μL of 10 mM glutamine in 0.1 M potassium phosphate (pH 7) were added and the assay mixture was incubated for 20 min at 37° C. A control experiment was carried out without substrate. The reaction was stopped at 95° C. for 10 min. The generated glutamic acid was calculated after HPLC analysis as described above.

ESI-Tandem MS Analysis of Tryptic Peptides

The peptidase bands were excised from SDS polyacrylamide gels, dried, and digested with trypsin. The resulting peptides were extracted and purified according to standard protocols. A Qtof II mass spectrometer (Micromass, U.K) equipped with a nanospray ion source and gold-coated capillaries was used for electrospray ionisation (ESI) MS of peptides. For collision-induced dissociation experiments, multiple charged parent ions were selectively transmitted from the quadrupole mass analyser into the collision cell (25-30 eV). The resulting daughter ions were separated by an orthogonal time-of-flight mass analyser. Peptide mass fingerprints obtained from ESI-Tandem MS analysis were used for cross-species protein identification in public protein primary sequence databases.

Native-PAGE and Denaturing SDS-PAGE

SDS-PAGE analyses were performed on a 12% polyacrylamide separation gel. Samples were prepared by mixing 20 μL of asparaginase enzyme solution and 20 μL of loading buffer [0.1 M Tris/HCl (pH 6.8), 0.2 M DTT, 4% SDS, 20% glycerol, 0.2% bromophenol blue] and boiling for 15 min. After electrophoresis at 20 mA per gel, the gels were stained with silver or Coomassie Brilliant Blue. For molecular determinations, marker proteins from 250 to 10 kDa (BioRad, Germany) were used.

Native PAGE was performed under non-denaturating conditions. Samples were prepared by mixing 1:1 (v/v) with loading buffer [0.05 M Tris/HCL (pH 6.8), 2% SDS, 10% glycerol, 0.1% bromophenol blue]. After electrophoresis at 10 mA per gel and at 8° C., gels were washed 2 times in 2.5% Triton X-100. The staining procedure is based on the deamidation of L-glutamine by glutaminase to produce L-glutamate. The oxidation of the L-glutamate by glutamate dehydrogenase is coupled to the reduction of a tetrazolium dye to its colored insoluble formazan. The glutaminase-staining solution contained 15 mM L-glutamine, 0.5 g mL$^{-1}$ bovine liver glutamate dehydrogenase, 0.1 M potassium phosphate pH 7, 2 mg mL$^{-1}$ NAD, 0.04 mg mL$^{-1}$ phenazine methosulfate, and 2 mg mL$^{-1}$ nitroblue tetrazolium. Enzyme activity appeared after incubation at 37° C. as violet bands.

Isoelectric Focusing

IEF polyacrylamide gel electrophoresis was performed on a Multiphor II system (Pharmacia LKB, Sweden) using Servalyt™ Precotes™ precast gels with an immobilised pH gradient from 3 to 10 (Serva, Germany) for 3500 V h (2000 V, 6 mA, 12 W). The isoelectric points of asparaginase were estimated to be 5 using a protein test mixture from pI 3.5 to 10.7 (Serva, Germany). Gels were Coomassie, silver or activity stained as described above.

RNA-Preparation

RNA was prepared from 500 mg mycelium stored in RNALater® (Invitrogen) using the NucleoSpin® RNA Plant Kit (Macherey-Nagel, Duren, Germany). cDNA-Synthesis 5 μg total RNA were mixed with 25 pmol 3'PCR (ATTCTAGAGGCCGAGGCGGCCGACATG 30*T VN) (SEQ ID NO: 2) and filled up to 11 μl with DEPC-treated H$_2$O. The mixture was incubated at 70° C. for 5 min and then chilled on ice for 2 min. 4 μl 5×reaction buffer, 2 μl dNTP mix (10 mM ea.), 0.5 μl RiboLock™ and 20 pmol SMART IIA (AAGCAGTGGTATCAACGCAGAGTACGCGGG) (SEQ ID NO: 3) were added, mixed and incubated at 37° C. for 5 min. After the addition of 200 U RevertAid™ H Minus M-MuLV Reverse Transcriptase the mixture was incubated at 42° C. for 60 min. Termination was carried out by heating at 70° C. for 5 min.

Second strand synthesis was carried out by mixing 2.5 μl 10×Long PCR buffer, 2 μl dNTP mix (2.5 mM ea.), 25 pmol 5'PCR (AAGCAGTGGTATCAACGCAGAGT) (SEQ ID NO: 4), 25 pmol 3'PCR, 1 μl DMSO, 1 U Long PCR Enzyme Mix, 3 μl ss cDNA and ddH$_2$O to 25 μl.

The reaction mixture was incubated at 94° C. for 5 min, followed by 30 cycles at 94° C. for 20 s and 68° C. for 6 min, final elongation was carried out at 68° C. for 20 min.

Enzymes and reagents were purchased from Fermentas, St. Leon-Rot, Germany. Oligonucleotides were synthesized by Eurofins MWG Operon, Ebersberg, Germany.

Sequence Fishing

Degenerated primers were deduced from peptide sequences. PCRs were performed by mixing 2.5 μl 10×TrueStart™ Taq-buffer, 2 μl dNTP mix (2.5 mM ea.), 2 μl 25 mM MgCl$_2$, 25 pmol forward primer, 25 pmol reverse primer, 0.8 μl DMSO, 0.625 U TrueStart™ Taq DNA Polymerase, 1 μl ds cDNA and ddH$_2$O to 25 μl.

Touchdown PCR [2] was performed by incubating the reaction mixture at 95° C. for 5 min, then for 12 cycles at 95° C. for 30 s, (72° C.-1° C./cycle) for 60 s and 72° C. for 90 s. Another 25 cycles were carried out at 60° C. annealing temperature. Final elongation was performed at 72° C. for 20 min.

PCRs were analyzed by agarose gel electrophoresis (1% agarose (Serva, Heidelberg, Germany) cooked in TAE-buffer (40 mM Tris, 20 mM acetic acid, 1 mM EDTA pH 8). For detection of DNA 0.05% SYBRSafe™ (Invitrogen) was added to the solution after it cooled down to about 50° C.

DNA extraction from agarose gels was carried out with the NucleoSpin Extract II Kit (Macherey-Nagel).

DNA fragments were ligated into the pCR2.1® TA-Vector (Invitrogen) by mixing 1 μl vector, 1 μl 10×T4 DNA Ligase-buffer, 5 U T4 DNA Ligase, 0.5 μl 5 mM ATP and 6.5 μl Insert-DNA. The reaction mixture was incubated at 25° C. for two hours.

For transformation 5 μl ligation reaction were added to 50 μl chemically competent *E. coli* TOP10 (Invitrogen), incubated on ice for 20 min, heat shocked at 42° C. for 45 s and transferred back on ice. 500 μl of SOC medium (Invitrogen) were added immediately. The cells were shaked at 200 rpm and 37° C. for 60 min and then plated on LB-agar containing 50 μg/ml ampicillin and 20 μg/ml X-Gal (Roth). Inoculated plates were incubated at 37° C. overnight. Selection of positive clones was performed by colony PCR. The reaction mixture was composed as stated above but primers M13 uni (-21) (TGTAAAACGACGGCCAGT) (SEQ ID NO: 5) and M13 rev (-29) (CAGGAAACAGCTATGACC) (SEQ ID NO: 6) were used. Template was added by resuspending white colony material in the reaction mixture.

The reaction mixture was incubated at 95° C. for 5 min, followed by 40 cycles at 95° C. for 30 s, 55° C. for 1 min and 72° C. for 1 min/kb. Final elongation was performed at 72° C. for 20 min.

Plasmid DNA was isolated with the NucleoSpin Plasmid DNA Kit (Macherey-Nagel). Sequencing was performed by Eurofins MWG Operon (Ebersberg, Germany).

In order to complete the sequence, specific primers were derived from identified asparaginase DNA fragments and paired with primers 5' PCR or 3' PCR, respectively. PCRs were carried out as stated above with an annealing temperature of 55° C. and an elongation step of 1 min at 72° C.

Amplification of the complete asparaginase sequence was achieved with primers FvNase-5' (ATGAAATCTTTTGCCCTCTTCG) (SEQ ID NO: 7) and FvNase-3' (TCAAGCAAAGTGATGAAGG) (SEQ ID NO: 8) at an annealing temperature of 55° C. and an elongation step of 1 min at 72° C.

To verify the sequence, genomic DNA was prepared from mycelium by using the Genomic DNA Purification Kit (Fermentas). The complete asparaginase sequence was amplified and sequenced.

Analysis of DNA and Amino Acid Sequence

Identification of an N-terminal signal sequence was carried out by analysis with Signal P 3.0 [3]. Sequence homology was investigated through a GenBank data base search using BLAST [4].

Heterologous Expression in *E. coli*

For cloning of asparaginase, the gene was amplified from the plasmid DNA by PCR with flanking restriction sites EcoRI and BamHI using the primers FvNase_EcoRI (ATAGAATTCATGAAATCTTTTGCCCTCTTC) (SEQ ID NO: 9) and FvNase_BamHI (ATAGGATCCTCAAGCAAAGTCGATGAA) (SEQ ID NO: 10). The gene cassette was digested and ligated into X-Zyme's pCTP2 expression vector to yield the expression construct pCTP2-Aspa. The *E. coli* strains DH5alpha and JM105 transformed with pCTP2-Aspa were grown in LB-medium at 37° C. to an OD$_{600\,nm}$ of 0.7, induced with 0.5 mM IPTG and further cultured overnight. Cells were resuspended in Tris-buffer pH 7.5, lysed with sonication and cell debris was removed by centrifugation. Purification of asparaginase was facilitated with ammonium sulphate.

Recombinant Asparaginase from *Bacillus subtilis*

The secretion of proteins from bacteria is an ATP-dependent process which involves the translocation of a pre-protein and the subsequent proteolytic cleavage of the pre-protein on the outside surface of the membrane, into the mature enzyme. A signal sequence contains all of the information necessary to target the protein to the membrane for translocation.

Although secretion in *Bacillus subtilis* is not as well understood as secretion in *E. coli*, it is generally assumed that it proceeds by the same mechanism (Saier, M. H., Jr., Werner, P. K. and Muller, M. 1989, Microbiol. Rev 53:333-366; Overhoff, B., Klein, M., Spies, M. and Freudl, R., 1991, Mol. Gen. Genet. 228:417-423). One difference between the two sets of secreted proteins is the length of their signal peptides which tend to be up to 20 amino acids longer in gram-positive than their corresponding gram-negative counterparts. Thus, the general strategy for the expression of heterologous proteins in gram-positive organisms such as *Bacillus subtilis* involves mating the target protein to the secretory apparatus of the host (Mountain, A., 1989, *Bacillus*, C. Harwood, ed., Plenum Press, New York, 73-114). Standard protocols using the above techniques are known in the art and were used for the overexpression of recombinant asparaginase by *Bacillus subtilis*.

Example 1

Cultivation of *Flammulina velutipes*

All media and equipment were autoclaved prior to use and standard sterile techniques were applied throughout the procedure. *Flammulina velutipes* was maintained on standard agar plates (30.0 g L$^{-1}$ glucose-monohydrate; 4.5 g L$^{-1}$ asparagine-monohydrate; 1.5 g L$^{-1}$ KH$_2$PO$_4$; 0.5 g L$^{-1}$ MgSO$_4$; 3.0 g L$^{-1}$ yeast extract; 15.0 g L$^{-1}$ agar agar; 1.0 mL L$^{-1}$ trace metal solution containing 0.005 g L1 CuSO$_4$.5H$_2$O, 0.08 g L$^{-1}$ FeCl$_3$.6H$_2$O, 0.09 g L$^{-1}$ ZnSO$_4$.7H$_2$O, 0.03 g L$^{-1}$ MnSO$_4$H$_2$O and 0.4 g L$^{-1}$ EDTA. The pH of the medium was adjusted to pH 6 with 1 M NaOH prior to sterilisation. Precultures were prepared by homogenisation of a 10×10 mm agar plug with mycelium of *Flammulina velutipes* in 100 mL of sterile standard nutrition solution using an Ultra Turrax (Miccra D-9, Art, Müllheim, Germany). Submerged cultures were maintained at 24° C. and 150 rpm. After cultivation for 5 days, 50 ml preculture were transferred into 250 ml main culture medium consisting of minimal medium (1.5 g L$^{-1}$ KH$_2$PO$_4$; 0.5 g L$^{-1}$ MgSO$_4$; 1.0 ml L$^{-1}$ trace metal solution) and 40 g L$^{-1}$ gluten or 10 mM glutamine, respectively.

Example 2

Enzyme Preparation from *Flammulina velutipes*

After 18 days of cultivation, the culture was filtrated and the extracellular enzyme-containing supernatant (200 mL) was reverse-foamed, the asparaginase and another protein being the only proteins left in the supernatant. The remaining liquid was concentrated using ultra-filtration (MWCO 10,000), and both proteins were separated via size exclusion chromatography at a Superose 6.

Most of the hydrolytic activity originally present was recovered indicating that this protocol yielded a useful enzyme concentrate through two steps only.

Example 3

Hydrolysis of L-Asparagine Using Native Enzyme

100 µL of 10 mM asparagine in 0.1 M K$_2$HPO$_4$/KH$_2$PO$_4$ buffer (pH 7.0) were preheated at 37° C. for 5 min. The reaction was started with the addition of 50 µL enzyme solution. After an incubation time of 20 min at 37° C. and 400 rpm in a thermoshaker, the assay was stopped by the addition of 20 µL TCA. A control experiment was carried out without substrate. The contents of aspartic acid were quantitatively measured with the HPLC after OPA-derivatisation, and the difference between sample and control was used to calculate then enzyme's activity.

The analytical evidence indicates a fast enzymatic hydrolysis of the substrate L-asparagine.

Example 4

Hydrolysis of L-Glutamine Using Native Enzyme

100 µL of 10 mM glutamine in 0.1 M K$_2$HPO$_4$/KH$_2$PO$_4$ buffer (pH 7.0) were preheated at 37° C. for 5 min. The reaction was started with the addition of 50 µl enzyme solution. After an incubation time of 20 min at 37° C. and 400 rpm in a thermoshaker, the assay was stopped by the addition of 20 µl TCA (Trichloroacetic acid). A control experiment was carried out without substrate. The contents of glutamic acid were quantitatively measured with the HPLC after OPA-derivatisation, and the difference between sample and control was used to calculate the enzyme's activity.

This analytical evidence indicated a useful side activity of the asparaginase towards the substrate L-glutamine.

Example 5

Hydrolysis of L-Asparagine Using Recombinant Enzyme

140 µl of 10 mM asparagine in 0.1 M K$_2$HPO$_4$/KH$_2$PO$_4$ buffer (pH 7.0) were preheated at 37° C. for 5 min. The reaction was started with the addition of 10 µl recombinant enzyme solution 200 times diluted with water. After an incubation time of 10 min at 37° C. and 400 rpm in a thermoshaker, the assay was stopped by heating at 95° C. for 10 min. A control experiment was carried out without substrate. The contents of aspartic acid were quantitatively measured with the HPLC after OPA-derivatisation, and the difference between sample and control was used to calculate the enzyme's activity. The activity of the recombinant asparaginase enzyme towards asparagine was calculated to be 43.3 kU L$^{-1}$.

Example 6

Hydrolysis of L-Glutamine Using Recombinant Enzyme

140 µL of 10 mM glutamine in 0.1 M K$_2$HPO$_4$/KH$_2$PO$_4$ buffer (pH 7.0) were preheated at 37° C. for 5 min. The reaction was started with the addition of 10 µl recombinant enzyme solution 200 times diluted with water. After an incubation time of 10 min at 37° C. and 400 rpm in a thermoshaker, the assay was stopped by heating at 95° C. for 10 min. Blanks were prepared without the substrate. The contents of glutamic acid were quantitatively measured with the HPLC after OPA-derivatisation, and the difference between sample and blank was used to calculate enzyme's activity. The activity of the recombinant asparaginase towards glutamine was calculated to be 4.3 kU L$^{-1}$.

Having thus described the present invention in detail, it is to be understood that the detailed description is not intended to limit the scope of the invention thereof.

The invention is claimed as follows:

1. A method for hydrolyzing at least one of L-asparagine or L-glutamine, the method comprising:
    treating a substance comprising at least one of L-asparagine or L-glutamine with an asparaginase enzyme comprising the amino acid sequence of SEQ ID NO: 1, thereby hydrolyzing said at least one of L-asparagine or L-glutamine; and
    inactivating said asparaginase enzyme by thermal treatment of said substance.

2. The method of claim 1, wherein said substance comprising at least one of L-asparagine or L-glutamine is at least one of a human consumable product or an animal consumable product.

3. The method of claim 1, wherein said substance is selected from the group consisting of beverages, cocoa beans, cheese, coffee beans, confectionary, desserts, dough, dressing, French fries, drinks, meat products, medical supplements, nutritional supplements, pet food, potato chips, sauces, snack and soups.

4. A method for reducing acrylamide formation in a food substance comprising L-asparagine, said method comprising:
    contacting said food substance comprising L-asparagine with an as asparaginase enzyme comprising the amino acid sequence of SEQ ID NO: 1, thereby reducing acrylamide formation in said food substance; and
    inactivating said asparaginase enzyme by thermal treatment of said food substance.

* * * * *

SEQUENCE LISTING

<160> NUMBER OF SEQ ID NOS: 12

<210> SEQ ID NO 1
<211> LENGTH: 123
<212> TYPE: PRT
<213> ORGANISM: Flammulina velutipes

<400> SEQUENCE: 1

Met Lys Ser Phe Ala Leu Phe Val Pro Leu Ile Val Ala Ala Val Val
1               5                   10                  15

Asn Ser Ala Val Val Thr Phe Ser Thr Gly Leu Gly Cys Asn Ser Val
            20                  25                  30

Ser Gln Thr Tyr Arg Gly Asn Gly Asn Phe Cys Ala Asp Pro Pro Gly
        35                  40                  45

Asp Trp Ser Ser Val Gly Phe Ser Glu Ile Gly Gly Asp Asn Arg Val
    50                  55                  60

Thr Val His Asn Gln Asn Ser Cys Thr Pro Ala Ser Gln Val Gly Gln
65                  70                  75                  80

Gly Phe Gly Pro Ala Cys Trp Asn Gln Gly Ala Thr Lys Leu Arg Ser
                85                  90                  95

Ala Trp Val Ala Cys Pro Gly Gln Arg Leu Ala Glu Asn Gly Thr Ile
            100                 105                 110

Val Asp Asp Gly Ala Phe Ile Asp Phe Ala
        115                 120

<210> SEQ ID NO 2
<211> LENGTH: 27
<212> TYPE: DNA
<213> ORGANISM: Artificial Sequence
<220> FEATURE:
<223> OTHER INFORMATION: Primer

<400> SEQUENCE: 2
attctagagg ccgaggcggc cgacatg                                              27

<210> SEQ ID NO 3
<211> LENGTH: 30
<212> TYPE: DNA
<213> ORGANISM: Artificial Sequence
<220> FEATURE:
<223> OTHER INFORMATION: Primer

<400> SEQUENCE: 3
aagcagtggt atcaacgcag agtacgcggg                                           30

<210> SEQ ID NO 4
<211> LENGTH: 23
<212> TYPE: DNA
<213> ORGANISM: Artificial Sequence
<220> FEATURE:
<223> OTHER INFORMATION: Primer

<400> SEQUENCE: 4
aagcagtggt atcaacgcag agt                                                  23

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5

-continued

```
tgtaaaacga cggccagt                                                 18

<210> SEQ ID NO 6
<211> LENGTH: 18
<212> TYPE: DNA
<213> ORGANISM: Artificial Sequence
<220> FEATURE:
<223> OTHER INFORMATION: Primer

<400> SEQUENCE: 6
caggaaacag ctatgacc                                                 18

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
atgaaatctt tgccctctt cg                                             22

<210> SEQ ID NO 8
<211> LENGTH: 19
<212> TYPE: DNA
<213> ORGANISM: Artificial Sequence
<220> FEATURE:
<223> OTHER INFORMATION: Primer

<400> SEQUENCE: 8
tcaagcaaag tgatgaagg                                                19

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9
atagaattca tgaaatcttt tgccctcttc                                    30

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
ataggatcct caagcaaagt cgatgaa                                       27

<210> SEQ ID NO 11
<211> LENGTH: 477
<212> TYPE: DNA
<213> ORGANISM: Flammulina velutipes

<400> SEQUENCE: 11
atgaaatctt tgccctctt cgtccctctc atcgttgctg ctgtcgtcaa cagcgccgtg    60 gtcaccttttt ccaccggcct tggctgcaac tctgtctcgc agacctaccg tgcaactgc   120 aacttctgcg ctgacccacc cggcggtagg tctacttcac attgatccct atagctgat   180 gctcatctca tctactagac tggagctcag tcggcttttc tgagatcgga ggcgacaacc   240
```

```
gcgtcaccgt tcataaccag aacagctgca cccccgcttc gcaggtcggc caaggctttg      300
gaccggcctg ctggaaccaa ggcgctacca agcttcgttc tgcttgggtt gcgtgccctg      360
gacagaggtg agtcggttct ctgcagcttc ttcttttggt ttactaacga tgccactaga      420
ctcgctgaga acggtaccat cgtcgacgac gacggcgcct tcatcgactt tgcttga        477

<210> SEQ ID NO 12
<211> LENGTH: 372
<212> TYPE: DNA
<213> ORGANISM: Flammulina velutipes

<400> SEQUENCE: 12
atgaaatctt ttgccctctt cgtccctctc atcgttgctg ctgtcgtcaa cagcgccgtg       60 gtcaccttt ccaccggcct tggctgcaac tctgtctcgc agacctaccg tggcaactgc      120
aacttctgcg ctgacccacc cggcgactgg agctcagtcg gcttttctga gatcggaggc      180
gacaaccgcg tcaccgttca taaccagaac agctgcaccc ccgcttcgca ggtcggccaa      240
ggctttggac cggcctgctg gaaccaaggc gctaccaagc ttcgttctgc ttgggttgcg      300
tgccctggac agagactcgc tgagaacggt accatcgtcg acgacgacgg cgccttcatc      360
gactttgctt ga                                                          372
```